(12) United States Patent
Sharonov

(10) Patent No.: US 11,553,974 B2
(45) Date of Patent: Jan. 17, 2023

(54) SYSTEMS AND METHODS FOR DETECTION OF OBJECTS WITHIN A FIELD OF VIEW OF AN IMAGE CAPTURE DEVICE

(71) Applicant: Covidien LP, Mansfield, MA (US)

(72) Inventor: Alexey Sharonov, Bethany, CT (US)

(73) Assignee: Covidien LP, Mansfield, MA (US)

( * ) Notice: Subject to any disclaimer, the term of this patent is extended or adjusted under 35 U.S.C. 154(b) by 322 days.

(21) Appl. No.: 16/615,522

(22) PCT Filed: May 8, 2018

(86) PCT No.: PCT/US2018/031590
§ 371 (c)(1),
(2) Date: Nov. 21, 2019

(87) PCT Pub. No.: WO2018/217444
PCT Pub. Date: Nov. 29, 2018

(65) Prior Publication Data
US 2020/0155254 A1    May 21, 2020

Related U.S. Application Data

(60) Provisional application No. 62/511,008, filed on May 25, 2017.

(51) Int. Cl.
*A61B 34/37*    (2016.01)
*A61B 90/00*    (2016.01)
(Continued)

(52) U.S. Cl.
CPC .............. *A61B 34/37* (2016.02); *A61B 90/37* (2016.02); *A61B 34/71* (2016.02);
(Continued)

(58) Field of Classification Search
CPC combination set(s) only.
See application file for complete search history.

(56) References Cited

U.S. PATENT DOCUMENTS 4,184,749 A    1/1980  Grossman
5,649,021 A    7/1997  Matey et al.
(Continued)

FOREIGN PATENT DOCUMENTS

JP    07328016    12/1995
JP    11174214    7/1999
(Continued)

OTHER PUBLICATIONS

Extended European Search Report dated Mar. 4, 2021 corresponding to counterpart Patent Application EP 18806900.9.
(Continued)

*Primary Examiner* — Scott Luan
(74) *Attorney, Agent, or Firm* — Carter, DeLuca & Farrell LLP

(57) ABSTRACT

Robotic surgical systems and methods of operating robotic surgical systems are included. The methods include directing light at an optical element configured to be detected by an image capture device of the robotic surgical system, the optical element configured to reflect light having a wavelength within a predetermined range, detecting, using an image capture device capturing images of the optical element, an absence or a presence of the reflected light from the optical element, and providing a notification, in response to the detection by the image capture device of the absence of the reflected light from the optical element.

16 Claims, 6 Drawing Sheets

(51) Int. Cl.
*A61B 34/20* (2016.01)
*A61B 34/00* (2016.01)

(52) U.S. Cl.
CPC . *A61B 2034/2055* (2016.02); *A61B 2034/742* (2016.02); *A61B 2034/743* (2016.02); *A61B 2034/744* (2016.02); *A61B 2090/3618* (2016.02); *A61B 2090/3937* (2016.02)

(56) References Cited

U.S. PATENT DOCUMENTS

| | | | |
|---|---|---|---|
| 6,132,368 A | 10/2000 | Cooper | |
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,324,011 B1 * | 11/2001 | Higuchi | G02B 5/124 |
| | | | 359/627 |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll et al. | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,927,694 B1 | 8/2005 | Smith et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco et al. | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez et al. | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,488,243 B2 | 7/2013 | McKnight et al. | |
| 8,499,992 B2 | 8/2013 | Whitman et al. | |
| 8,508,173 B2 | 8/2013 | Goldberg et al. | |
| 8,528,440 B2 | 9/2013 | Morley et al. | |
| 8,529,582 B2 | 9/2013 | Devengenzo et al. | |
| 8,540,748 B2 | 9/2013 | Murphy et al. | |
| 8,551,116 B2 | 10/2013 | Julian et al. | |
| 8,562,594 B2 | 10/2013 | Cooper et al. | |
| 8,594,841 B2 | 11/2013 | Zhao et al. | |
| 8,597,182 B2 | 12/2013 | Stein et al. | |
| 8,597,280 B2 | 12/2013 | Cooper et al. | |
| 8,600,551 B2 | 12/2013 | Itkowitz et al. | |
| 8,608,773 B2 | 12/2013 | Tierney et al. | |
| 8,620,473 B2 | 12/2013 | Diolaiti et al. | |
| 8,624,537 B2 | 1/2014 | Nowlin et al. | |
| 8,634,957 B2 | 1/2014 | Toth et al. | |
| 8,638,056 B2 | 1/2014 | Goldberg et al. | |

(56) References Cited

U.S. PATENT DOCUMENTS

| | | |
|---|---|---|
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,830,329 B2 | 9/2014 | Mao et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrisse, I et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |

(56) References Cited

U.S. PATENT DOCUMENTS

| | | |
|---|---|---|
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 2006/0149418 A1 | 7/2006 | Anvari |
| 2009/0088634 A1 | 4/2009 | Zhao et al. |
| 2009/0245600 A1 | 10/2009 | Hoffman et al. |
| 2012/0116365 A1 | 5/2012 | Price et al. |
| 2013/0030571 A1 | 1/2013 | Ruiz Morales et al. |
| 2013/0128011 A1 | 5/2013 | Tu et al. |
| 2014/0121834 A1* | 5/2014 | Ogawa .................. A61B 34/30 700/257 |
| 2015/0005622 A1 | 1/2015 | Zhao et al. |
| 2015/0049952 A1 | 2/2015 | Cholayil et al. |
| 2016/0183930 A1 | 6/2016 | Herzlinger et al. |
| 2016/0256225 A1 | 9/2016 | Crawford et al. |

FOREIGN PATENT DOCUMENTS

| | | |
|---|---|---|
| JP | 2008529707 A | 8/2008 |
| JP | 2009542362 A | 12/2009 |
| JP | 2010200894 A | 9/2010 |
| JP | 2011125687 A | 6/2011 |
| JP | 2013022651 A | 2/2013 |
| KR | 1020110049703 | 5/2011 |
| KR | 20120122643 A | 11/2012 |
| WO | 2008002830 A2 | 1/2008 |
| WO | 2009/023801 A1 | 2/2009 |
| WO | 2013012018 A1 | 1/2013 |

OTHER PUBLICATIONS

Japanese Office Action dated Jan. 11, 2022 corresponding to counterpart Patent Application JP 2019-564993.

International Search Report dated Nov. 8, 2018 and Written Opinion completed Nov. 7, 2018 corresponding to counterpart Int'l Patent Application PCT/US18/31590.

Japanese Office Action dated Jan. 31, 2022 corresponding to counterpart Patent Application JP 2019-564889.

Indian Office Action dated Mar. 28, 2022 issued in corresponding IN Appln. No. 201917047199.

Indian Office Action dated Feb. 24, 2022 issued in corresponding IN Appln. No. 201917047198.

Fobii, e-book, tech.tobii.com. Copyright 2021, Tobii AB, "5 Ways Next-Generation Surgical Robotics Will Leverage Attention to Enhance Care", p. 1/12 -12/12.

Fobii, Tobii White Paper, tech.tobii.com., May 2020, Version 1.0, "Why Next-Generation Surgical Systems Will Include Eye Tracking", p. 1/15-p. 15/15.

Japanese Office Action dated Jul. 29, 2022 issued in corresponding JP Appln. No. 201880006826.5.

Japanese Notice of Allowance dated Aug. 18, 2022 issued in corresponding JP Appln. No. 2019-564993.

Chinese Office Action dated Aug. 22, 2022 issued in corresponding CN Appln. No. 201880033983.5.

Japanese Office Action dated Sep. 6, 2022 issued in corresponding JP Appln. No. 2019-564889.

* cited by examiner

SYSTEMS AND METHODS FOR DETECTION OF OBJECTS WITHIN A FIELD OF VIEW OF AN IMAGE CAPTURE DEVICE

CROSS-REFERENCE TO RELATED APPLICATIONS

This application is a National Stage Application of PCT/US2018/031590, filed May 8, 2018 under 35USC § 371 (a), which claims benefit of and priority to U.S. Provisional Patent Application Ser. No. 62/511,008 filed May 25, 2017, the disclosures of each of the above-identified applications are hereby incorporated by reference in their entirety.

BACKGROUND

Robotic surgical systems are increasingly being used in minimally invasive medical procedures. Typically, robotic surgical systems include a surgeon console located remote from one or more robotic arms to which surgical instruments and/or cameras are coupled. The surgeon console may be located on another side of the operating room from the robotic arms, in another room, or in another building, and includes input handles or other input devices for receiving inputs from a surgeon. The inputs are communicated to a central controller, which translates the inputs into commands for manipulating the robotic arms in the vicinity of the patient.

To view a surgical site, the surgeon console may include a stereoscopic display, sometimes referred to as a three-dimensional (3D) display. In some configurations, in conjunction with a corresponding pair of stereoscopic eyeglasses worn by the surgeon, such displays facilitate depth perception in an image by presenting the image to the surgeon as a pair of distinct images separately provided to the left and right eyes, respectively, replicating the effect of the offset between the left and right eyes, which results in a difference in what is seen in the display by each eye. The different images seen in the display by each eye are perceived as differences in the depths of the objects in the images. In other configurations, the stereoscopic display is viewed without the need for eyeglasses.

The surgeon console may further include a camera positioned to capture images of the surgeon. The captured images may be used to track eye or head position of the surgeon to detect instances in which the surgeon is not looking at the display. In some configurations of the robotic system, the central controller may generate signals or block generated signals to prevent the movement of instruments, in response to the detected eye or head position of the surgeon.

SUMMARY

Robotic surgical systems and methods for operating robotic surgical systems are provided. According to an aspect of the present disclosure, the robotic surgical system includes a robotic arm, a surgeon console, a processor, and a memory. The surgeon console includes a light source, an optical element configured to reflect light having a wavelength within a predetermined range, an image capture device configured to detect the light reflected by the optical element, and a notification device configured to provide a notification. The processor is operatively coupled to the robotic arm and in communication with the console. The memory has instructions stored thereon, which when executed by the processor, cause the processor to detect by the image capture device an absence or a presence of the light reflected by the optical element, and cause the notification device to provide the notification, in response to the image capture device detecting the absence of the light reflected by the optical element.

In another aspect of the present disclosure, the robotic surgical system of includes a wearable device including the optical element.

In another aspect of the present disclosure, the optical element includes a diffusive/reflective element.

In another aspect of the present disclosure, the diffusive/reflective element includes a plurality of partitions. In still another aspect of the present disclosure, the optical element includes a film including a transparency having a reflective element configured to reflect light having a wavelength within the predetermined range.

In still another aspect of the present disclosure, the optical element includes a film including a transparency having a first diffusive element configured to reflect light having a wavelength within a first predetermined range to permit a first shape to be visually perceived and a second diffusive element configured to reflect light having a wavelength within a second predetermined range to permit a second shape to be visually perceived, and the image capture device is configured to detect the first shape and the second shape, and the notification device is further configured to provide the notification, in response to the image capture device detecting the absence of the first shape.

In another aspect of the present disclosure, the surgeon console further includes an input handle, and the memory has further instructions stored thereon, which when executed by the processor, cause the processor to generate a signal, in response to a manipulation of the input handle, and disable the input handle, in response to the image capture device detecting the absence of the light reflected by the optical element. In still another aspect of the present disclosure, the memory has further instructions stored thereon, which when executed by the processor, cause the processor to disable the input handle, in response to the image capture device detecting the absence of the light reflected by the optical element for a time period greater than a threshold time period.

In another aspect of the present disclosure, the memory has further instructions stored thereon, which when executed by the processor, cause the processor to cause the notification device to provide the notification, in response to the image capture device detecting the absence of the light reflected by the optical element for a time period greater than a threshold time period.

In accordance with another aspect of the present disclosure, a method of operating a robotic surgical system is provided and includes directing light at an optical element configured to be detected by an image capture device of the robotic surgical system, the optical element configured to reflect light having a wavelength within a predetermined range, detecting, using an image capture device capturing images of the optical element, an absence or a presence of the reflected light from the optical element, and providing a notification, in response to the detection by the image capture device of the absence of the reflected light from the optical element.

In another aspect of the present disclosure, the optical element is disposed on a wearable device.

In another aspect of the present disclosure, the optical element includes a diffusive/reflective element.

In another aspect of the present disclosure, the diffusive/reflective element includes a plurality of partitions.

In another aspect of the present disclosure, the optical element includes a film including a transparency having a reflective element configured to reflect light having a wavelength within the predetermined range.

In another aspect of the present disclosure, the optical element includes a film including a transparency having a first diffusive element configured to reflect light having a wavelength within a first predetermined range to permit a first shape to be visually perceived and a second diffusive element configured to reflect light having a wavelength within a second predetermined range to permit a second shape to be visually perceived, and the method further includes detecting an absence or presence of the first shape and the second shape, using the image capture device, and providing the notification, in response to the image capture device detecting the absence of the first shape.

In another aspect of the present disclosure, the method further includes generating a signal, in response to a manipulation of an input handle of the robotic surgical system, and disabling the input handle, in response to the image capture device detecting the absence of the light reflected by the optical element.

In another aspect of the present disclosure, the method further includes disabling the input handle, in response to the image capture device detecting the absence of the light reflected by the optical element for a time period greater than a threshold time period.

In another aspect of the present disclosure, the method further includes causing the notification device to provide the notification, in response to the image capture device detecting the absence of the light reflected by the optical element for a time period greater than a threshold time period.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION

Figure 1:
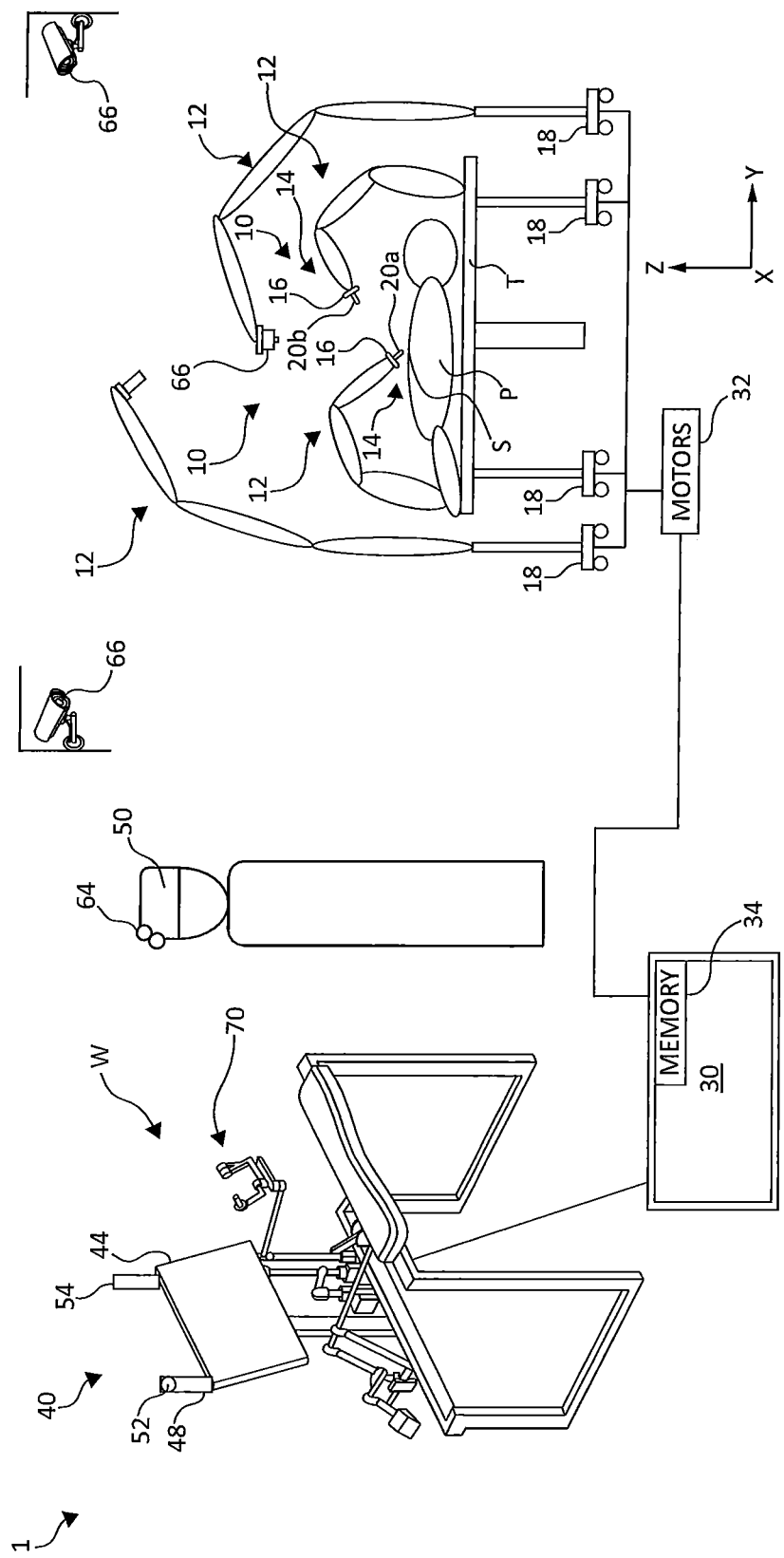
FIG. 1 is a schematic illustration of a robotic surgical system, in accordance with the present disclosure.

The present disclosure employs optical elements or markers and cameras or image capture devices to determine a position of an object or a person. As will be described in greater detail below, when the markers are detected by the camera or image capture devices, the locations of the detected markers are used to calculate the position of the object or person. Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is farthest from the patient and the term "distal" refers to the portion of the device or component thereof that is closest to the patient.

With reference to FIG. 1, a robotic surgical system 10 is provided, which is configured for use on a patient "P" lying on an operating table "T" for the performance of a minimally invasive surgical operation. In accordance with an embodiment, the robotic surgical system 10 generally includes a plurality of robotic arms 12 configured to receive commands from a controller 30 for manipulating one or more of the robotic arms 12 in response to an input received at a remotely-located surgeon console 40.

Each of the robotic arms 12 is made up of a plurality of members connected through joints coupled to and extending from a base 18. Each base 18 provides different locations from which each robotic arm 12 extends. For example, the base 18 may be made up of a plurality of movable carts. In another embodiment, all of the robotic arms 12 extend from a single base. In an embodiment, connected to a distal end of each robotic arm 12 is a surgical assembly 14, which includes a surgical instrument holder 16 that is configured to removably couple with a surgical instrument 20. Each robotic arm 12 may include a surgical instrument 20 configured for a different purpose. For example, one robotic arm 12 may include a surgical instrument including a grasping jaw instrument 20, while another robotic arm 12 may include a surgical instrument including scissors. Other suitable instruments 20a, 20b include, but are not limited to, staplers, clip appliers, suture passers, spatulas, and the like.

Although four robotic arms 12 are depicted, the surgical system 10 may include fewer or more than four robotic arms 12. In this regard, the additional robotic arms (not shown) are likewise connected to the controller 30 and are telemanipulatable via the console 40. Accordingly, one or more additional surgical assemblies 14, surgical instrument holders 16, and/or surgical instruments 20a, 20b may also be attached to the additional robotic arms. In another embodiment, one or more of the robotic arms 12 includes an image capture device 66 positioned over the surgical site "S", an image capture device 66 disposed in the surgical site "S" (not shown) or the like. The image capture devices 66 capture visual images, infra-red images, ultrasound images, X-ray images, thermal images, and/or any other known real-time images of the surgical site "S". In still another embodiment, one or more of the image capture devices 66 are not attached to the robotic arms 12 and are placed at predetermined locations around the operating room. In any case, the image capture devices 66 transmit captured imaging data to the controller 30 which creates images of the surgical site "S" and/or the operating room in real-time from the imaging data and transmits the images to the display device 44 for display. In another embodiment, the displayed images are two-dimensional renderings of the data captured by the image capture devices.

The robotic arms 12 may be driven by electric drives (not shown) that are connected to the controller 30. According to an embodiment, the controller 30 is configured to activate drives, for example, via a computer program, such that the robotic arms 12 and the surgical assemblies 14, surgical instrument holders 16, and/or surgical instruments 20*a*, 20*b* corresponding to the robotic arms 12, execute a desired movement received through the console 40. The controller 30 may also be configured to regulate movement of the robotic arms 12 and/or of the drives.

The controller 30 may control a plurality of motors 32 with each motor configured to drive a pushing or a pulling of one or more cables, such as cables (not shown) coupled to the surgical instrument 20. In use, as these cables are pushed and/or pulled, the one or more cables effect operation and/or movement of the surgical instruments 20*a*, 20*b*. The controller 30 coordinates the activation of the various motors 32 to coordinate a pushing or a pulling motion of one or more cables in order to coordinate an operation and/or movement of one or more surgical instrument 20. In an embodiment, each motor 32 is configured to actuate a drive rod or a lever arm to effect operation and/or movement of surgical instruments 20*a*, 20*b* in addition to, or instead of one or more cables.

The controller 30 includes any suitable logic control circuit adapted to perform calculations and/or operate according to a set of instructions. The controller 30 can be configured to communicate with a remote system (not shown) either via a wireless (e.g., Wi-Fi, Bluetooth, LTE, etc.) and/or wired connection. The remote system can include data, instructions and/or information related to the various components, algorithms, and/or operations of console 40. The remote system can include any suitable electronic service, database, platform, cloud, or the like. The controller 30 may include a central processing unit operably connected to memory 34. The memory may include transitory type memory (e.g., RAM) and/or non-transitory type memory (e.g., flash media, disk media, etc.). In some embodiments, the memory is part of, and/or operably coupled to, the remote system.

The controller 30 can include a plurality of inputs and outputs for interfacing with the components of the console 40, such as through a driver circuit. The controller 30 can be configured to receive input signals and/or generate output signals to control one or more of the various components (e.g., one or more motors and/or the display device 44) of the console 40. The output signals can include, and/or can be based upon, algorithmic instructions which may be pre-programmed and/or input by a user. The controller 30 can be configured to accept a plurality of user inputs from a user interface (e.g., switches, buttons, touch screen, etc. of operating the console 40) which may be coupled remote to the system 10.

The memory 34 can be directly and/or indirectly coupled to the controller 30 to store instructions and/or databases including pre-operative data from living being(s) and/or anatomical atlas(es). The memory 34 can be part of, and/or or operatively coupled to, the remote system 10.

To provide the input to the controller 30, the surgeon console 40 includes various input devices. In an embodiment, the surgeon console 40 includes input handles 70 or input pedals configured to be manipulated by the surgeon through actuation. In particular, the surgeon uses his or her hands to grip and move the input handles 70 and the movement of the input handles 70 are translated via the controller 30 to thereby provide a corresponding movement to the robotic arms 12 and/or surgical instruments 20*a*, 20*b*. The surgeon steps on the input pedals to provide a selection to provide further controls of the robotic arms 12 or the surgical instruments 20*a*, 20*b*.

The display device 44 is set up to display two- or three-dimensional images received from the image capture devices 66. In an embodiment in which three-dimensional images are provided, the display device 44 is configured to provide the three-dimensional images for viewing either with or without specialized viewing lenses provided, for example, in the form of a head set 50, such as one configured as glasses or another suitable configuration.

The head set 50 includes markers 64 disposed thereon. In an embodiment, the detection of the markers 64 indicates that the eyes of the surgeon wearing the head set 50 are directed at the display device 44. The markers 64 on the head set 50 may be configured in a similar manner to those included on the surgical assemblies 14, surgical instrument holders 16, surgical instruments 20*a*, 20*b*, and/or the distal end of the robotic arm 12. According to an embodiment, the one or more markers 64 are placed at specific locations on the head set 50 such that detection of the markers 64 indicates that the surgeon's head is positioned in a particular manner, for example, looking forward at the display device 44. To detect the markers 64, the surgeon console 40 includes an image capture device 48 mounted to the display device 44 or at another location to allow the image capture device 48 to be directed at the surgeon during system operation. The image capture device 48 may include one or more filters 52, such as a band pass optical filter, for the detection of the markers 64, in an embodiment.

Figure 2:
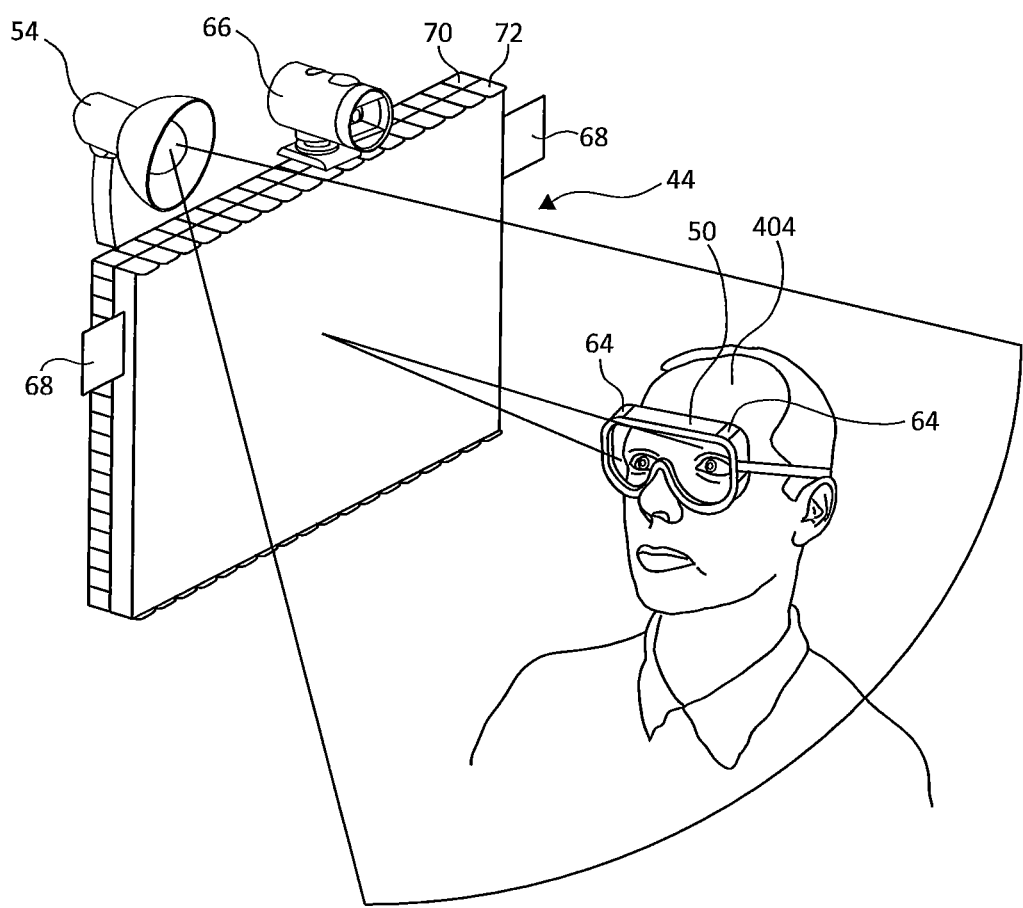
FIG. 2 is a perspective view of a portion of a display system for implementation into the robotic surgical system of FIG. 1, in accordance with the present disclosure.

FIG. 2 is a perspective view of a portion of a display system for implementation into the robotic surgical system 10, showing an example arrangement of the display device 44, the head set 50, a light source 54, the image capture device 48, and audio devices 68, in accordance with various embodiments herein. In an embodiment, the display device 44 includes a screen 70 and one or more layers 72 disposed in front of the screen 70. The screen 70 includes pixels that direct visual content displayed by certain pixels to certain eyes of the surgeon by way of the one or more layers 72. In particular, the one or more layers 72 may include a lenticular lens layer. For example, the lenticular lens layer includes a plurality of vertical lenses disposed over corresponding pixel rows configured to be directed at an angle suitable to permit the visual content of a first set of pixels to be perceived by a first eye of the surgeon and a second set of pixels to be perceived by a second eye of the surgeon.

A light source 54 is configured to provide light and may be mounted along an edge of the display device 44 (as illustrated in FIG. 1) or positioned adjacent, above or below the display device 44. The light source 54 may provide light in the visible and/or invisible spectrum (such as ultraviolet, infrared or the like) to be reflected by markers 64, which may be included at predetermined locations on the head set 50. The markers 64 may be optical elements including mechanisms to permit the visibility of reflected light when viewed at an angle that is within a predetermined range of angles, in accordance with an embodiment, for detection by the image capture device 48. In an embodiment, the display system is configured such that a notification is provided audibly, for example, by the audio devices 68, tactilely or visually via the display device 44, if the markers 64 are not detected.

Figure 4:
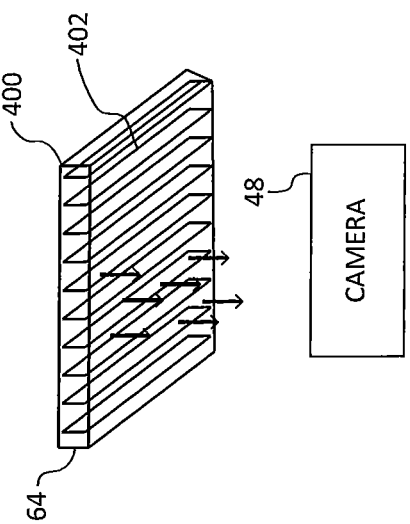
FIG. 4 is a simplified view of a marker and an image capture device for use in robotic surgical system of FIG. 1, in accordance with another embodiment.
Figure 3:
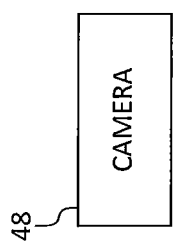
FIG. 3 is a simplified view of a marker and an image capture device for use in robotic surgical system of FIG. 1, in accordance with an embodiment.
Figure 3:
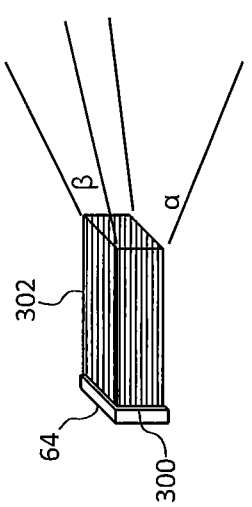

As illustrated in FIG. 3, the marker 64 is made up of a reflective element 300 and a diffusive element 302. The reflective element 300 may include a mirror, and the diffusive element 302 may be a tube-shaped element having a rectangular cross-sectional shape, to permit limiting the visibility of the marker 64 by the image capture device 48 by restricting the light reflected by the reflective element 300. Specifically, travel of the reflected light may be restricted horizontally by a first angle β and vertically by a second angle α. Although depicted as having a rectangular cross-sectional shape, the tube-shaped element may have a different cross section shape. In another embodiment, as illustrated in FIG. 4, the marker 64 includes a reflective element 400 and a diffusive element 402, which includes a plurality of tube-shaped elements having rectangular cross-sectional shapes. The tube-shaped elements are substantially identical to each other extending in the same direction and cooperate to limit the light reflected by the reflective element 400 to allow the marker 64 to be detected by the image capture device 48.

Figure 5:
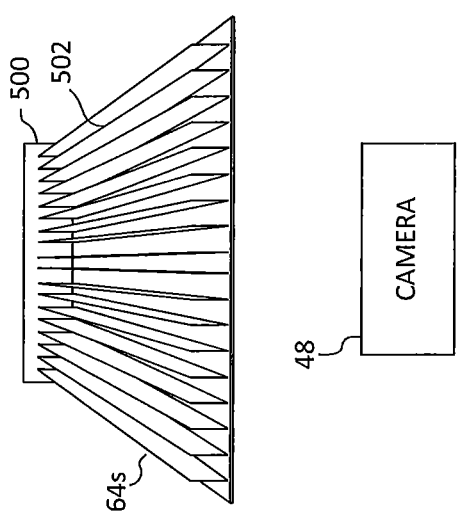
FIG. 5 is a simplified view of a marker and an image capture device for use in robotic surgical system of FIG. 1, in accordance with still another embodiment.

In accordance with another embodiment, the markers 64 may be optical elements including mechanisms to permit the visibility of reflected light when viewed at an angle that is within a predetermined range of angles, for example, as depicted in FIG. 5. Here, the marker 64 has a reflective element 500 and a diffusive element 502, where the diffusive element 502 is in the form of a film with a transparency configured to limit viewing of the marker 64 to the predetermined range of angles. In an embodiment, the diffusive element 502 is configured to allow light directed within a range relative to the reflective element 500 to reflect (for example, a range of viewing angles including an angle substantially perpendicular to the reflective element 500) and to thereby be visible to the image capture device 48. Light directed at the diffusive element 502 at an angle that is outside of the range of viewing angles is not reflected by the reflective element 500 and hence, is not visible to the image capture device 48.

Figure 6:
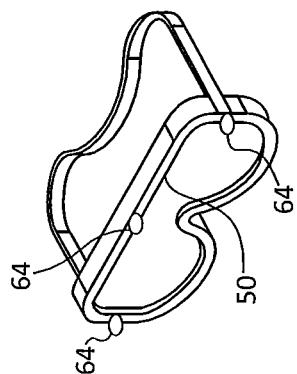
FIG. 6 is a simplified view of a marker on a headset and an image capture device for use in robotic surgical system of FIG. 1, in accordance with an embodiment.
Figure 6:
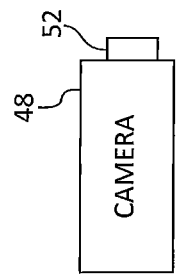

In another embodiment, as depicted in FIG. 6, the markers 64 are configured to reflect light within a particular range of wavelengths (for example, visible or invisible). In such an embodiment, the image capture device 48 includes a bandpass optical filter 52 selected to correspond to the particular range of wavelengths of the markers 64. Thus, the image capture device 48 detects the markers 64 when the wavelength of light reflected from the markers 64 passes through the bandpass optical filter 52 thereby permitting the image capture device 48 to view the markers 64. The markers 64 are illustrated as being disposed on a head set 50 in the form of a pair of eyeglasses, in this embodiment. It will be appreciated that the markers 64 alternatively may be included on a headband or other wearable or may be stickers that are placed on various locations of the user's face or head.

Figure 7:
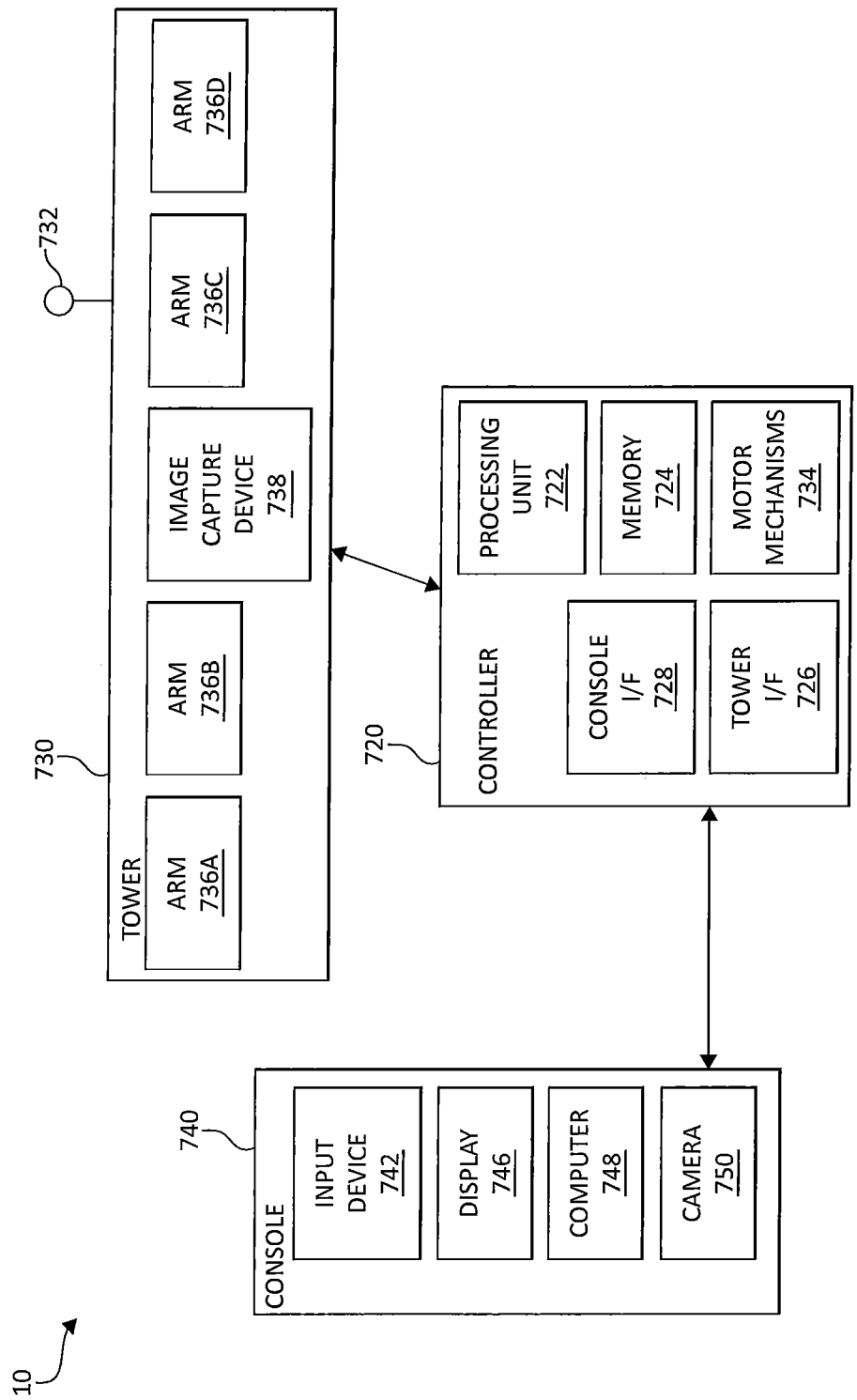
FIG. 7 is functional block diagram of the robotic surgical system, in accordance with the present disclosure.

FIG. 7 is simplified block diagram of the robotic surgical system 10 of FIG. 1. The robotic surgical system 10 includes a controller 720, a tower 730, and a console 740. The controller 720 is configured to communicate with the tower 730 to thereby provide instructions for operation, in response to input received from the console 740.

The controller 720 generally includes a processing unit 722, a memory 724, a tower interface 726, and a console interface 728. The processing unit 722, in particular by means of a computer program stored in the memory 724, functions in such a way to cause components of the tower 730 to execute a desired movement according to a movement defined by input devices 742 of the console 740. In this regard, the processing unit 722 includes any suitable logic control circuit adapted to perform calculations and/or operate according to a set of instructions. The processing unit 722 may include one or more processing devices, such as a microprocessor-type of processing device or other physical device capable of executing instructions stored in the memory 724 and/or processing data. The memory 724 may include transitory type memory (e.g., RAM) and/or non-transitory type memory (e.g., flash media, disk media, etc.). The tower interface 726 and console interface 728 communicate with the tower 730 and console 740, respectively, either wirelessly (e.g., Wi-Fi, Bluetooth, LTE, etc.) and/or via wired configurations. Although depicted as separate modules, the interfaces 732, 734 may be a single component in other embodiments.

The tower 730 includes a communications interface 732 configured to receive communications and/or data from the tower interface 726 for manipulating motor mechanisms 734 to thereby move robotic arms 736a-736d. In accordance with an embodiment, the motor mechanisms 734 are configured to, in response to instructions from the processing unit 722, receive an application of current for mechanical manipulation of cables (not shown) which are attached to the robotic arms 736a-736d to cause a desired movement of a selected one of the robotic arms 736a-736d and/or an instrument coupled to one of the robotic arms 736a-736d. The tower 730 also includes an image capture device 738, which captures real-time images and transmits data representing the images to the controller 730 via the communications interface 732.

To aid the surgeon in manipulating the devices of the tower 730, the console 740 has an input device 742, a display 746, a computer 748, and a camera 750. The input device 742 is coupled to the computer 748 and is used by the clinician to provide an input. In this regard, the input device 742 may be a handle or pedal, or other computer accessory, such as a keyboard, joystick, mouse, button, trackball or other component. The computer 748 includes a processing unit and memory, which includes data, instructions and/or information related to the various components, algorithms, and/or operations of the tower 730 and can operate using any suitable electronic service, database, platform, cloud, or the like. The display 746 receives instructions from the computer 748 to display information received from the image capture device 738 and/or from the communications interface 732. The camera 750 captures images of the surgeon at the console 740.

Figure 8:
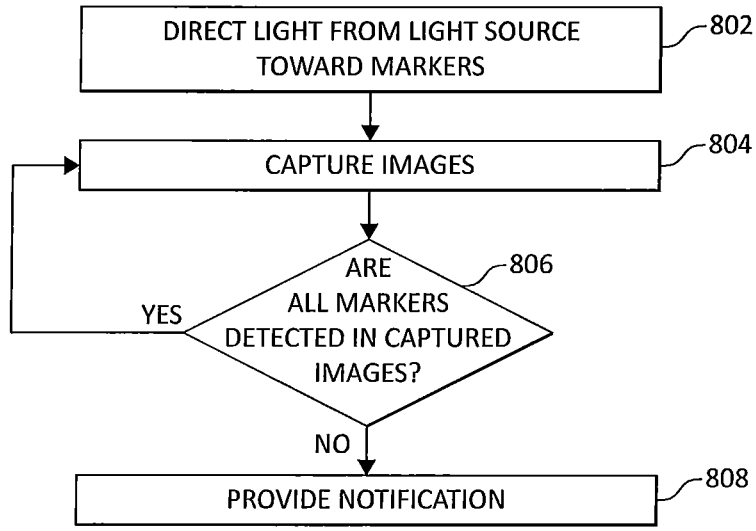
FIG. 8 is a flow diagram of a method for determining positions of a surgeon relative to a display device of the robotic surgical system, in accordance with the present disclosure.

The markers 64 described briefly above are useful for implementing various positioning and safety mechanisms. In an example, during surgery, it may be advantageous for the system 10 to be aware of the positioning of the surgeon relative to the display device 44. Turning now to FIG. 8, a flow diagram of a method 800 is provided for determining the positioning of the surgeon relative to the display device 44 of the robotic surgical system 10, in accordance with an embodiment. The method 800 may be implemented, at least in part, by the processing unit 722 executing instructions stored in the memory 724 (FIG. 7). Additionally, the particular sequence of steps shown in the method 800 of FIG. 8 is provided by way of example and not limitation. The steps of the method 800 may be executed in sequences other than the sequence shown in FIG. 8 without departing from the scope of the present disclosure. Further, some steps shown in the method 800 of FIG. 8 may be concurrently executed instead of sequentially executed.

With reference to FIG. 8, light from the light source 54 is directed toward the markers 64 at step 802. As noted above, the markers 64 are disposed on the surgeon's head or face, for example, on the head set 50. Thus, depending on the positioning of the surgeon's head or face, the markers 64 may or may not reflect the light from the light source 54. For example, in an embodiment, a plurality of the markers 64 are included on the head set 50 at specific locations such that detection of all of the markers 64 indicates that the surgeon's eyes are directed at the display device 44. In another embodiment, the marker or markers 64 at least partially cover the head set 50 to form a specific shape, and detection of the specific shape indicates that the surgeon's eyes are directed at the display device 44.

In any case, to determine whether the one or more markers 64 are detected, the image capture device 48 captures images of the surgeon at step 804. Based on the images from step 804, a determination is made as to whether all of the markers 64, whether they be a plurality of the markers 64 disposed at the specific locations or one or more markers 64 forming a specific shape, are detected at step 806. If the markers 64 are detected, the method 800 iterates a step 804 to capture additional images of the surgeon using the image capture device 48. If all of the markers 64 are not detected, a notification is provided by the system 10 at step 808 indicating that the surgeon's eyes are not directed at the display device 44. The notification may be provided after a time period threshold has been surpassed, in an embodiment. For example, the notification may begin after the markers 64 are undetected for a period, such as 1 second, 3 seconds, and the like. The time period may be longer or shorter in other embodiments. In an example, the system 10 may provide an audible notification, via audio devices 68, a tactile notification and/or a visual notification. In accordance with an embodiment, in addition to providing the notification, the system 10 prevents inputs from being received at the input handles 70 or other input devices, such as pedals (if included).

Figure 9:
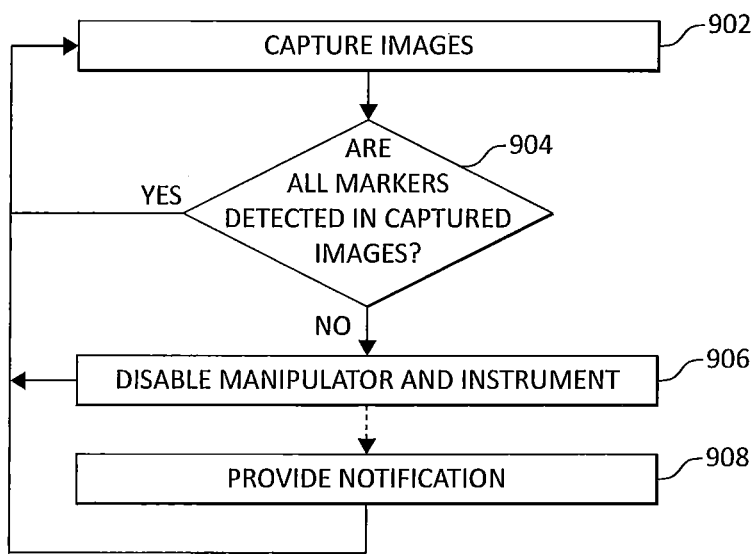
FIG. 9 is a flow diagram of another method for determining the position of a surgeon relative to a display device of the robotic surgical system, in accordance with the present disclosure.

In another example of using the markers 64, in order to provide additional control of the robotic arms 12, the system 10 is configured to further prevent unintended movement by using one or more markers on the head set 50 worn by the surgeon to determine whether the surgeon's eyes are directed at the display device 44. In this regard, the system 10 is configured to capture image data including the head set 50 (on which the one or more markers 64 are disposed) via the camera 48 and to detect the markers 64 within the captured image data. Turning now to FIG. 9 is, a flow diagram of a method 900 of determining a position of the surgeon's head relative to the display device 44 is provided, in accordance with an embodiment. The method 900 may be implemented, at least in part, by the processing unit 722 executing instructions stored in the memory 724 (FIG. 7). Additionally, the particular sequence of steps shown in the method 900 of FIG. 9 is provided by way of example and not limitation. The steps of the method 900 may be executed in sequences other than the sequence shown in FIG. 9 without departing from the scope of the present disclosure. Further, some steps shown in the method 900 of FIG. 9 may be concurrently executed instead of sequentially executed.

In an embodiment, images of the surgeon are captured by the camera 48 at step 902. A determination is then made as to whether one or more of the markers 64 are detected in the captured images, at step 904. In an embodiment, the camera 48 is configured to detect whether the marker(s) 64 are within its field of view and positioned at a particular angle or location relative thereto. The detection of the markers 64 indicates that the eyes of the surgeon wearing the head set 50 on which the markers 64 are disposed are directed at the display device 44. In an embodiment, the markers 64 include diffusive and/or reflective material, and the camera 48 includes a corresponding filter 52 to allow visual perception of the marker 64 only when the marker 64 is presented at a certain angle. The markers 64 include those types in which the visibility of an optical target is restricted by walls or partitions thereby permitting the optical target to be visually perceived only when viewed at the certain angles. In another example, the markers 64 are constructed from a front surface mirror covered with an engineered transparency film limited to a specific range of angles within which light will be reflected. In another example, the markers 64 include a reflective material covered with an engineered diffuser to limit visibility of the markers 64 to specific angles in horizontal and/or vertical planes, such as those sold by ThorLabs of Newton, N.J. Thus, when the head set 50 worn by the surgeon is tilted at an angle permitting the light reflected off of the markers 64 and filtered through the filter 52 on the camera 48 to be visible to the camera 48, the markers 64 are then detected. Otherwise, the markers 64 are not detected.

If a determination is made that the marker(s) 64 on the head set 50 are not detected, the system 10 disables movement of the robotic arms 12 and instruments 20a, 20b at step 906. In an example, inputs received from the input handles 70 are not communicated to the robotic arms 12 or instruments 20a, 20b. For example, when the surgeon actuates or moves the input handles 70, either signals are not generated or, if generated, the signals are not communicated to the robotic arms 12 and/or instruments 20a, 20b. In this way, when the surgeon is not looking at the display device 44, the system 10 is prevented from allowing operations which may affect the patient "P." The disabling may occur after a time period threshold has been surpassed, in an embodiment. For example, the disabling may begin after the markers 64 are undetected for a period, such as 1 second, 3 seconds, and the like. The time period may be longer or shorter in other embodiments. Optionally, a notification is provided at step 908, either on the display device 44, audibly or tactilely to indicate that the surgeon should re-position his or her head to re-enable the functions of the robotic arms 12 and/or instruments 20a, 20b. If a determination is made that the markers 64 are not detected within the field of view of the camera 48, the systems 10 permits operation of the robotic arms 12 and instruments 20a, 20b as usual and iterates at step 902 to capture additional images.

In accordance with an embodiment, the disabling and enabling of the movement of the robotic arms 12 and/or instruments 20a, 20b depends on whether one of the markers 64 is detected. In another embodiment, the disabling and enabling of the movement of the robotic arms 12 and/or instruments 20a, 20b depends on whether all of the markers 64 included in a set of markers 64 on the head set 50 is detected.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs)

and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A robotic surgical system comprising:
   a robotic arm;
   a surgeon console including:
      a light source,
      an optical element configured to reflect light having a wavelength within a predetermined range, the optical element includes a film including a transparency having a first diffusive element configured to reflect light having a wavelength within a first predetermined range to permit a first shape to be visually perceived and a second diffusive element configured to reflect light having a wavelength within a second predetermined range to permit a second shape to be visually perceived,
      a notification device configured to provide a notification, and
      an image capture device configured to detect the light reflected by the optical element, the image capture device is configured to detect the first shape and the second shape, and the notification device is further configured to provide the notification, in response to the image capture device detecting the absence of the first shape;
   a processor operatively coupled to the robotic arm and in communication with the console; and
   a memory having instructions stored thereon, which when executed by the processor, cause the processor to:
      detect by the image capture device an absence or a presence of the light reflected by the optical element, and
      cause the notification device to provide the notification, in response to the image capture device detecting the absence of the light reflected by the optical element.

2. The robotic surgical system of claim 1, further comprising a wearable device including the optical element.

3. The robotic surgical system of claim 2, wherein the optical element includes a diffusive/reflective element.

4. The robotic surgical system of claim 3, wherein the diffusive/reflective element includes a plurality of partitions.

5. The robotic surgical system of claim 3, wherein the optical element includes a film including a transparency having a reflective element configured to reflect light having a wavelength within the predetermined range.

6. The robotic surgical system of claim 1, wherein:
   the surgeon console further includes an input handle, and
   the memory has further instructions stored thereon, which when executed by the processor, cause the processor to:
      generate a signal, in response to a manipulation of the input handle, and
      disable the input handle, in response to the image capture device detecting the absence of the light reflected by the optical element.

7. The robotic surgical system of claim 6, wherein the memory has further instructions stored thereon, which when executed by the processor, cause the processor to:
   disable the input handle, in response to the image capture device detecting the absence of the light reflected by the optical element for a time period greater than a threshold time period.

8. The robotic surgical system of claim 1, wherein the memory has further instructions stored thereon, which when executed by the processor, cause the processor to:
   cause the notification device to provide the notification, in response to the image capture device detecting the absence of the light reflected by the optical element for a time period greater than a threshold time period.

9. A method of operating a robotic surgical system, the method comprising:
   directing light at an optical element configured to be detected by an image capture device of the robotic surgical system, the optical element configured to reflect light having a wavelength within a predetermined range, the optical element includes a film including a transparency having a first diffusive element configured to reflect light having a wavelength within a first predetermined range to permit a first shape to be visually perceived and a second diffusive element configured to reflect light having a wavelength within a second predetermined range to permit a second shape to be visually perceived;
   detecting, using an image capture device capturing images of the optical element, an absence or a presence of the reflected light from the optical element;

providing a notification on a notification device, in response to the detection by the image capture device of the absence of the reflected light from the optical element;
detecting an absence or presence of the first shape and the second shape, using the image capture device; and
providing the notification, in response to the image capture device detecting the absence of the first shape.

10. The method of claim 9, wherein the optical element is disposed on a wearable device.

11. The method of claim 9, wherein the optical element includes a diffusive/reflective element.

12. The method of claim 11, wherein the diffusive/reflective element includes a plurality of partitions.

13. The method of claim 11, wherein the optical element includes a film including a transparency having a reflective element configured to reflect light having a wavelength within the predetermined range.

14. The method of claim 9, further comprising:
generating a signal, in response to a manipulation of an input handle of the robotic surgical system; and
disabling the input handle, in response to the image capture device detecting the absence of the light reflected by the optical element.

15. The method of claim 14, further comprising:
disabling the input handle, in response to the image capture device detecting the absence of the light reflected by the optical element for a time period greater than a threshold time period.

16. The method of claim 9, further comprising:
causing the notification device to provide the notification, in response to the image capture device detecting the absence of the light reflected by the optical element for a time period greater than a threshold time period.

* * * * *